United States Patent [19]

Kirstgen et al.

[11] Patent Number: 5,403,838

[45] Date of Patent: Apr. 4, 1995

[54] α-ARYLACRYLIC ACID DERIVATIVES, THEIR PREPARATION AND USE FOR CONTROLLING PESTS AND FUNGI

[75] Inventors: Reinhard Kirstgen, Neustadt; Hans Theobald; Hartmann Koenig, both of Limburgerhof; Albrecht Harreus, Ludwigshafen; Klaus Oberdorf, Heidelberg; Uwe Kardorff, Mannheim; Volker Harries, Frankenthal; Gisela Lorenz, Neustadt; Eberhard Ammermann, Heppenheim, all of Germany

[73] Assignee: BASF Aktiengesellschaft, Ludwigshafen, Germany

[21] Appl. No.: 928,038

[22] Filed: Aug. 11, 1992

[30] Foreign Application Priority Data

Aug. 16, 1991 [DE] Germany .................. 41 26 994.2

[51] Int. Cl.$^6$ .............. C07D 213/30; C07D 307/12; C07D 261/20
[52] U.S. Cl. ................... 514/224.2; 514/340; 514/378; 514/403; 514/275; 514/341; 548/215; 548/240; 548/373.1; 548/374.1; 548/372.1; 548/375.1; 548/365.7; 548/365.4; 548/364.1; 548/312.4; 548/377.1
[58] Field of Search ............ 548/367, , 215, 240, 548/373.1; 514/224.2, 340, 378, 403, 341, 275

[56] References Cited

FOREIGN PATENT DOCUMENTS

| | | |
|---|---|---|
| 0034754 | 9/1981 | European Pat. Off. . |
| 0087953 | 9/1983 | European Pat. Off. . |
| 0178826 | 4/1986 | European Pat. Off. . |
| 203606 | 2/1988 | European Pat. Off. . |
| 0256667 | 2/1988 | European Pat. Off. . |
| 229974 | 11/1988 | European Pat. Off. . |
| 0335519 | 10/1989 | European Pat. Off. . |
| 0378755 | 7/1990 | European Pat. Off. . |
| 0402246 | 12/1990 | European Pat. Off. . |

OTHER PUBLICATIONS

Abstract of E.P.A. 5159d, 2 Dec. 1992.
Abstract of E.P.A. 51380, 19 Nov. 1992.
Journal Of The Chemical Society, Perkin Transactions (List continued on next page.)

*Primary Examiner*—Thurman K. Page
*Assistant Examiner*—Peter F. Kulkosky
*Attorney, Agent, or Firm*—Oblon, Spivak, McClelland, Maier & Neustadt

[57] ABSTRACT

α-Arylacrylic acid derivatives of the formula I

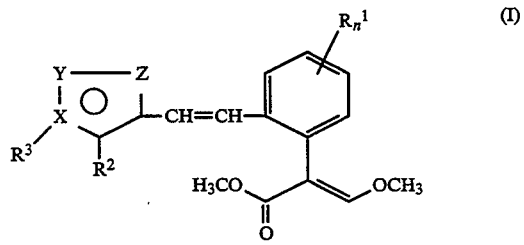

where the substituents have the following meanings:
X C, N
Y CR$^4$, N, O, S
Z CR$^5$, N, O, S
n 0 to 4
R$^1$ hydrogen, nitro, cyano, halogen; alkyl, alkoxy, halogenated alkyl, halogenated alkoxy or alkylthio, or, when n is 2, 3 or 4, two adjacent substituents R$^1$ may together denote a 1,3-butadien-1,4-diyl group which may be substituted;
R$^2$ alkyl; halogenated alkyl, halogen, cyano, nitro, alkoxycarbonyl, dimethylamino, R$^2$ additionally denotes hydrogen;
R$^3$ hydrogen; substituted or unsubstituted alkyl; a substituted or unsubstituted cyclic structure, which may contain, in addition to carbon atoms, one to three heteroatoms; or a substituted or unsubstituted aromatic system, which may contain, in addition to carbon atoms, one to four nitrogen atoms and one to three heteroatoms;
R$^4$, R$^5$ hydogen, alkyl; halogenated alKyl, halogen, cyano, nitro, dimethylamino, alkoxycarbonyl
and pesticides and fungicidal agents containing these compounds.

24 Claims, No Drawings

OTHER PUBLICATIONS 1, pp. 2047–2057, 1989, M. J. Crimmin, et al., "The Chemistry of Pseudomonic Acid. Part 10. ¹Preparation of Heterocyclic Derivatives".

Journal of The Chemical Society, Perkin Transactions 1, pp. 2893–2987, 1982, B. P. Giovanni, et al., "Asymmetric Synthesis of a Beta-Ketol Moiety Via 3,5-Disubstituted Isoxazoles: Application to (+)-(S)-[6]-Gingerol".

Journal of Organic Chemistry, vol. 48, No. 7, pp. 1149–1150, Apr. 1983, L. A. Paquette, et al., "Methodology for the Synthesis of 3-Acyltetramic Acids".

α-ARYLACRYLIC ACID DERIVATIVES, THEIR PREPARATION AND USE FOR CONTROLLING PESTS AND FUNGI

The present invention relates to α-arylacrylic acid derivatives of the general formula I $$\text{(I)}$$

where
X is C or N,
Y is $CR^4$, N, O or S,
Z is $CR^5$, N, O or S, Y and Z not simultaneously being O, S or O and S,
n is from 0 to 4,
$R^1$ is nitro, cyano, halogen;
$C_1$-$C_4$-alkyl, $C_1$-$C_4$-alkoxy, partially or completely halogenated $C_1$-$C_4$-alkyl, partially or completely halogenated $C_1$-$C_4$-alkoxy or $C_1$-$C_4$-alkylthio,
or, where n is 2, 3 or 4, two adjacent substituents $R^1$ together form 1,3-butadiene-1,4-diyl, which may carry from one to four halogen atoms and/or one or two of the following groups: nitro, cyano, $C_1$-$C_4$-alkyl, $C_1$-$C_4$-alkoxy, partially or completely halogenated $C_1$-$C_4$-alkyl, partially or completely halogenated $C_1$-$C_4$-alkoxy or $C_1$-$C_4$-alkylthio; $R^2$ is $C_1$-$C_4$-alkyl, partially or completely halogenated $C_1$-$C_4$-alkyl, halogen, cyano, nitro, $C_1$-$C_4$-alkoxycarbonyl or dimethylamino, and $R^2$ may additionally be hydrogen, in which case $R^3$ is a heterocyclic or heteroaromatic radical or $R^4$ or $R^5$ is not hydrogen;
$R^3$ is hydrogen;
unsubstituted or substituted alkyl;
an unsubstituted or substituted saturated or monounsaturated or diunsaturated cyclic structure which, in addition to carbon atoms, may contain from one to three hetero atoms selected from the group consisting of oxygen, sulfur and nitrogen as ring members; or an unsubstituted or substituted mononuclear or dinuclear aromatic system which, in addition to carbon atoms, may contain from one to four nitrogen atoms or from one to three hetero atoms selected from a group consisting of two nitrogen atoms and one oxygen or sulfur atom, and
$R^4$ and $R^5$ are each hydrogen, $C_1$-$C_4$-alkyl, partially or completely halogenated $C_1$-$C_4$-alkyl, halogen, cyano, nitro, dimethylamino or $C_1$-$C_6$-alkoxycarbonyl.

The present invention furthermore relates to processes for the preparation of these compounds and agents containing them, and methods for controlling pests and fungi.

The literature discloses α-arylacrylic acid derivatives as fungicides (EP-A 203 606, EP-A 229 974), as insecticides and fungicides (EP-A 178 826, EP 378 755) and as insecticides (EP-A 256 667, EP-A 335 519).

It is an object of the present invention to provide novel effective insecticides and fungicides.

We have found that this object is achieved by the α-arylacrylic acid derivatives I defined at the outset.

We have also found processes for the preparation of these α-arylacrylic acid derivatives and agents containing them, as well as methods for their use.

Owing to the two —C=C— groups in the molecule, the novel compounds can occur in the form of cis- and trans-isomers. Both the individual isomers and mixtures thereof are biologically active and form the subject of the invention. Preferred compounds are those in which both —C=C— groups are in the E configuration.

The α-arylacrylic acid derivatives I are obtainable by various methods, for example those described in the literature cited at the outset. They are particularly advantageously obtained by the Processes A and B described below.

Process A:

The α-arylacrylic acid derivatives of the formula I are obtained, for example, by reacting a triphenylphosphonium salt or a phosphonic ester of the general formula II (for example according to EP-A 203 606 or J. Am. Chem. Soc. 83 (1961), 1732) with aldehyde of the general formula III in an inert organic solvent in the presence of a base.

In the formula II, R is $C_1$-$C_8$-alkyl, in particular methyl, ethyl, propyl or 1-methylethyl.

The reaction is carried out in general at from $-30°$ to $60°$ C., preferably from $0°$ to $40°$ C.

Examples of suitable solvents are diethyl ether, benzene, toluene, tetrahydrofuran, dimethoxyethane, methanol, ethanol and dimethylformamide.

Tetrahydrofuran and dimethylformamide are particularly suitable.

The bases used in this process are n-butyllithium, sodium hydride, sodium methylate, potassium tert-butylate, sodium tert-amylate, lithium dimethylamide and lithium bistrimethylsilylamide.

The preparation of the required intermediates is described, for example, in the literature cited at the outset.

A triphenylphosphonium salt is, for example, of the following formula

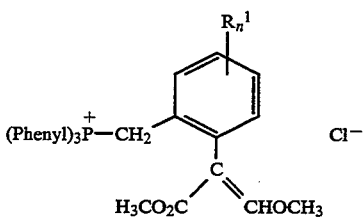

Process B:

The α-arylacrylic acid derivatives of the formula I are also obtained, for example, by reacting a triphenylphosphonium salt or a phosphonic ester of the general formula IV with the benzaldehyde V in an inert organic solvent in the presence of a base.

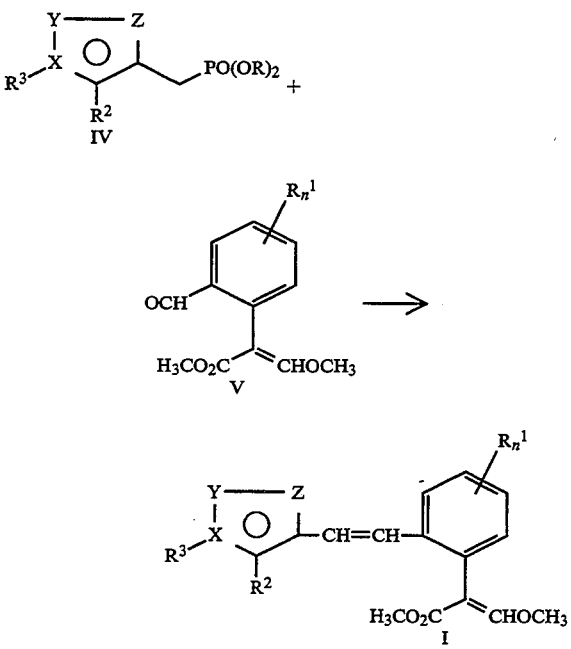

In the formula IV, R is $C_1$-$C_8$-alkyl, in particular methyl, ethyl, propyl or 1-methylethyl.

The reaction is carried out in general at from $-30°$ to $60°$ C., preferably from $0°$ to $40°$ C.

Suitable solvents and suitable bases are in general and in particular those stated for Process A.

A triphenylphosphonium salt is, for example, of the following formula

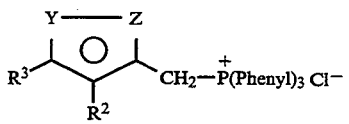

In view of the intended use of the compounds I in insecticides and fungicides, particularly suitable substituents are the following radicals:
X is C or N,
Y is CH, $CR^4$, N, O or S,
Z is CH, $CR^5$, N, O or S,
n is from 0 to 4,
$R^1$ is nitro; cyano;

halogen, such as fluorine, chlorine, bromine or iodine, preferably fluorine, chlorine or bromine, in particular fluorine or chlorine;

branched or straight-chain $C_1$-$C_4$-alkyl, such as methyl, ethyl, propyl, 1-methylethyl, butyl, 1-methylpropyl, 2-methylpropyl or 1,1-dimethylethyl, preferably methyl, ethyl, 1-methylethyl or 1,1-dimethylethyl, in particular methyl or 1,1-dimethylethyl;

$C_1$-$C_4$-alkoxy, such as methoxy, ethoxy, propoxy, 1-methylethoxy, butoxy, 1-methylpropoxy, 2-methylpropoxy or 1,1-dimethylethoxy, preferably methoxy, ethoxy or 1,1-dimethylethoxy, in particular methoxy;

partially or completely halogenated $C_1$-$C_4$-alkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably dichloromethyl, trichloromethyl or trifluoromethyl, in particular trifluoromethyl;

partially or completely halogenated $C_1$-$C_4$-alkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, 1,1,2,2-tetrafluoroethoxy or pentafluoroethoxy, preferably trichloromethoxy, difluoromethoxy, trifluoromethoxy, chlorodifluoromethoxy or 1,1,2,2-tetrafluoroethoxy, in particular difluoromethoxy or 1,1,2,2-tetrafluoroethoxy, or $C_1$-$C_4$-alkylthio, such as methylthio, ethylthio, propylthio, 1-methylethylthio, butylthio, 1-methylpropylthio, 2-methylpropylthio or 1,1-dimethylethylthio, preferably methylthio or ethylthio, in particular methylthio, or, where n is 2, 3 or 4, 1,3-butadiene-14-diyl, which may carry from one to four halogen atoms, such as fluorine, chlorine, bromine or iodine, preferably fluorine or chlorine, in particular chlorine and/or one or two of the following groups:

nitro, cyano, straight-chain or branched $C_1$-$C_4$-alkyl, such as methyl, ethyl, propyl, 1-methylethyl, butyl, 1-methylpropyl, 2-methylpropyl or 1,1-dimethylethyl, preferably methyl or ethyl, in particular methyl, $C_1$-$C_4$-alkoxy, such as methoxy, ethoxy, propoxy, 1-methylethoxy, butoxy, 1-methylpropoxy, 2-methylpropoxy or 1,1-dimethylethoxy, preferably methoxy or ethoxy in particular methoxy, partially or completely halogenated $C_1$-$C_4$-alkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably trifluoromethyl, partially or completely halogenated $C_1$-$C_4$-alkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2- difluoroethoxy, 2,2-dichloro-2-fluoroethoxy, 2,2,2-trichloroethoxy or pentafluoroethoxy, preferably difluoromethoxy or 1,1,2,2-tetrafluoroethoxy, in particular difluoromethoxy, or $C_1$-$C_4$-alkylthio, such as methylthio, ethylthio, propylthio, 1-methylethylthio, butylthio, 1-methylpropylthio, 2-methylpropylthio or 1,1-dimethylethylthio, preferably methylthio;

$R^2$ is nitro; cyano; dimethylamino;

halogen as stated above, preferably fluorine, chlorine or bromine, in particular chlorine or bromine;

branched or straight-chain $C_1$-$C_4$-alkyl as stated above, in particular methyl, 1-methylethyl, 1-methylpropyl or 1,1-dimethylethyl; partially or completely halogenated $C_1$-$C_4$-alkyl as stated preferably and in particular above; straight-chain or branched $C_1$-$C_6$-alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl, pentyloxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexyloxycarbonyl, 1,1-dimethylpropoxycarbonyl, 1,2-dimethylpropoxycarbonyl, 1-methylpentyloxycarbonyl, 2-methylpentyloxycarbonyl, 3-methylpentyloxycarbonyl, 4-methylpentyloxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, preferably $C_1$-$C_4$-alkoxycarbonyl, in particular methoxycarbonyl, ethoxycarbonyl or 1,1-dimethylethoxycarbonyl;

unsubstituted or substituted alkyl radicals $R^3$ in the general formula I are straight-chain or branched alkyl of not more than 12 carbon atoms, in particular $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, propyl or 1-methylethyl, in particular methyl, ethyl, propyl, butyl or 1,1-dimethylethyl, where these groups may be partially or completely halogenated.

Among the partially or completely halogenated alkyl groups, preferred ones are those which carry from one to nine halogen atoms as stated above, preferably fluorine, chlorine or bromine, in particular chlorine or fluorine.

The stated alkyl groups $R^3$ may furthermore carry from one to four of the following radicals:

cyano; cyanato; thiocyanato; nitro;

straight-chain or branched $C_1$-$C_6$-alkoxy, such as methoxy, ethoxy, n-propoxy, 1-methylethoxy, n-butoxy, 1-methylpropoxy, 2-methylpropoxy, 1,1-dimethylethoxy, n-pentyloxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, preferably $C_1$-$C_4$-alkoxy, in particular $C_1$- or $C_2$-alkoxy.

In the general formula I, unsubstituted or substituted saturated or monounsaturated or diunsaturated cyclic structures $R^3$ which, in addition to carbon atoms, may contain from one to three hetero atoms as ring members, selected from a group consisting of two nitrogen atoms and one oxygen or sulfur atom, are saturated or monounsaturated or diunsaturated nonaromatic ring systems having not more than eight ring members, in particular $C_3$-$C_8$-cycloalkyl, such as cyclopropyl, cyclobutyl, cyclopentyl, cyclohexyl, cycloheptyl or cyclooctyl, preferably cyclopropyl, cyclopentyl or cyclohexyl, in particular cyclopropyl;

$C_5$-$C_8$-cycloalkenyl, such as cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclooct-1-enyl, cyclooct-2-enyl, cyclooct-3-enyl or cyclooct-1-enyl, preferably cyclopent-1-enyl, cyclopent-3-enyl or cyclohex-1-enyl, in particular cyclopent-3-enyl;

$C_5$-$C_8$-cycloalkadienyl, such as cyclopenta-1,3-dien-1-yl, cyclopenta-1,3-dien-2-yl, cyclopenta-1,3-dien-5-yl, cyclohexa-1,3-dien-1-yl, cyclohexa-1,3-dien-2-yl, cyclohexa-1,3-dien-5-yl, cyclohexa-1,4-dien-1-yl, cyclohexa-1,4-dien-3-yl, cyclohepta-1,3-dien-1-yl, cyclohepta-1,3-dien-2-yl, cyclohepta-1,3-dien-5-yl, cyclohepta-1,3-dien-6-yl, cyclohepta-1,4-dien-1-yl, cyclohepta-1,4-dien-2-yl, cyclohepta-1,4-dien-3-yl, cyclohepta-1,4-dien-6-yl, cycloocta-1,3-dien-1-yl, cycloocta-1,3-dien-2-yl, cycloocta-1,3-dien-5-yl, cycloocta-1,3-dien-6-yl, cycloocta-1,4-dien-1-yl, cycloocta-1,4-dien-2-yl, cycloocta-1,4-dien-3-yl, cycloocta-1,4-dien-6-yl, cycloocta-1,4-dien-7-yl, cycloocta-1,4-dien-1-yl or cycloocta-1,4-dien-3-yl, preferably cyclopenta-1,3-dien-5-yl;

a 3-membered to 6-membered, saturated or partially unsaturated heterocyclic structure containing from one to three nitrogen atoms or from one to three hetero atoms selected from a group consisting of two nitrogen atoms, two oxygen atoms and two sulfur atoms or from a group consisting of three oxygen and sulfur atoms, such as epoxidyl, 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4- thiadiazolidin-2-yl, 1,3,4-triazolidin-2-yl,2,3-dihydrofur-2-yl, 2,3-dihydrofur-3-yl, 2,5-dihydrofur-2-yl, 2,5-dihydrofur-3-yl,2,3-dihydrothien-2-yl,2,3-dihydrothien-3-yl, 2,5-dihydrothien-2-yl, 2,5-dihydrothien-3-yl, 2,3-pyrrolin-2-yl, 2,3-pyrrolin-3-yl, 2,4-pyrrolin-2-yl, 2,5-pyrrolin-3-yl, 2,3-isoxazolin-3-yl, 3,4-isoxazolin-3-yl, 4,5-isoxazolin-3-yl,2,3-isoxazolin-4-yl,3,4-isoxazolin-4-yl, 4,5-isoxazolin-4-yl, 2,3-isoxazolin-5-yl, 3,4-isoxazolin-5-yl,4,5-isoxazolin-5-yl,2,3-isothiazolin-3-yl, 3,4-isothiazolin-3-yl, 4,5-isothiazolin-3-yl, 2,3-isothiazolin- 4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol -1-yl, 2,3-dihydropyrazol-2-yl, 2,3-dihydropyrazol-3-yl, 2,3-dihydropyrazol-4-yl, 2,3-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, oxazol-2-in-2-yl, 2-tetrahydropyranyl, 1,3-dioxolan-2-yl, thiazol-2-in-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, N-morpholinyl or dihydroquinazolinyl, in particular 2-oxazolidinyl, 1,3-dihydrooxazin-2-yl, 2-oxazolin-2-yl, oxiranyl, 2-tetrahydrofuranyl, 1,3-dithian-2-yl, 2-tetrahydropyranyl or 1,3-dioxolan-2-yl, where these groups may furthermore carry from one to three radicals selected from a group consisting of halogen as stated above, preferably fluorine, chlorine and bromine, in particular fluorine and chlorine, cyano; nitro, dimethylamino;

straight-chain or branched $C_1$-$C_6$-alkyl as stated in general and in particular above;

$C_1$-$C_4$-alkoxy as stated in general and in particular above;

$C_1$-$C_4$-alkylthio as stated in general and in particular above;

$C_3$-$C_8$-cycloalkyl as stated in general and in particular above;

phenyl, and where the heterocyclic radicals may additionally carry a number of halogen atoms as stated above, preferably fluorine, chlorine or bromine, in particular fluorine or chlorine, such that the total number of radicals is 4 or 5.

In the general formula I, unsubstituted or substituted mononuclear or dinuclear aromatic systems $R^3$ which, in addition to carbon atoms, may contain from one to four nitrogen atoms or one or two nitrogen atoms and one oxygen or sulfur atom are aromatic and heteroaromatic ring systems having not more than 10 ring members, in particular phenyl, 1-naphthyl or 2-naphthyl, in particular phenyl, five-membered heteroaromatic structures containing from one to three hetero atoms selected from a group consisting of three nitrogen atoms and one oxygen or sulfur atom, such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-triazol-2-yl, 1,3,4-oxadiazol-2-yl, 1,3,4-thiadiazol-2-yl, 1,3,4-triazol-3-yl, 1,2,3-oxadiazol-4-yl, 1,2,3-oxadiazol-5-yl, 1,2,5-triazol-3-yl, 1,2,3-triazol-4-yl, 1,2,3-triazol-5-yl, 1,2,3-triazol-4-yl, 1,2,3,4-thiatriazol-5-yl or 1,2,3,4-oxatriazol-5-yl, in particular 3-pyrrolyl, 3-isoxazolyl, 5-isoxazolyl, 2-furyl, 2-thienyl, 4-oxazolyl, 4-thiazolyl, 4-pyrazolyl, 5-pyrazolyl, 1,3,4-oxadiazol-2-yl or 1,3,4-thiadiazol-2-yl, or six-membered heteroaromatic structures containing from one to four nitrogen atoms as hetero atoms, such as 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl or 1,2,4,5-tetrazin-3-yl, in particular 2-pyridyl, 3-pyridyl, 2-pyrimidinyl, 4-pyrimidinyl or 1,3,5-triazin-2-yl, where these groups may carry from one to five halogen atoms as stated above, preferably fluorine, chlorine or bromine, in particular fluorine or chlorine, and/or from one to four of the following radicals:

cyano; cyanato; thiocyanato; nitro; amino; hydroxyl; carboxyl;

$C_1$-$C_6$-alkyl as stated in general and in particular above; partially or completely halogenated $C_1$-$C_4$-alkyl as stated in general and in particular above;

$C_1$-$C_6$-alkoxy as stated in general and in particular above; partially or completely halogenated $C_1$-$C_4$-alkoxy as stated in general and in particular above;

$C_1$-$C_6$-alkylthio as stated in general and in particular above;

$C_3$-$C_8$-cycloalkyl as stated in general and in particular above;

$C_1$-$C_6$-alkoxycarbonyl as stated in general above, preferably $C_1$-$C_4$-alkoxycarbonyl;

phenyl and phenoxy.

The abovementioned phenyl radicals may in turn carry from one to three substituents selected from a group consisting of halogen as stated in general and in particular above;

cyano; nitro;

$C_1$-$C_4$-alkyl as stated in general and in particular above; partially or completely halogenated $C_1$-$C_4$-alkyl as stated in general and in particular above;

$C_1$-$C_4$-alkoxy as stated in general and in particular above; partially or completely halogenated $C_1$-$C_4$-alkoxy as stated in general and in particular above and $C_1$-$C_4$-alkylthio as stated in general and in particular above, and the abovementioned phenyl radicals may additionally carry a number of halogen atoms as stated in general and in particular above such that the total number of their radicals is 4 or 5.

$R^4$ and $R^5$ are each, for example, hydrogen; nitro; cyano; dimethylamino;

halogen as stated above, preferably fluorine, chlorine or bromine, in particular chlorine or bromine;

branched or straight-chain $C_1$-$C_4$-alkyl as stated above, in particular methyl, 1-methylethyl, 1-methylpropyl or 1,1-dimethylethyl;

partially or completely halogenated $C_1$-$C_4$-alkyl as stated preferably and in particular above;

or straight-chain or branched $C_1$-$C_6$-alkoxycarbonyl as stated preferably and in particular above.

Because of their biological activity against pests and fungi, compounds of the general structure I in which the substructure

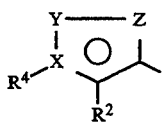

is one of the following radicals

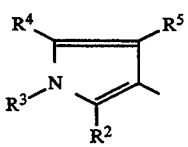

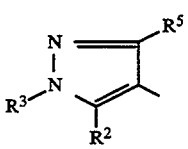

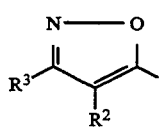

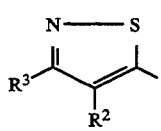

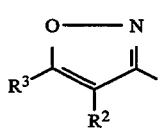

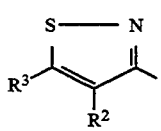

are preferred.

PREPARATION EXAMPLE I

Preparation of methyl
α-2-[2-(5-methyl-1-phenylpyrazol-4-yl)-ethen-1-yl]-phenyl-β-methoxyacrylate (Example No. 2.18)

A solution of 7.9 g of dimethyl 2-(β-methoxy-α-methoxycarbonylvinyl)-benzylphosphonate and 5.1 g of 5-methyl-1-phenylpyrazol-4-ylcarboxaldehyde in 80 ml of tetrahydrofuran is added dropwise to a suspension of 0.7 g of sodium hydride in 25 ml of anhydrous tetrahydrofuran at room temperature. The internal temperature should not exceed 30° C. The mixture is further stirred overnight and then hydrolyzed with ice water and extracted with methyl tert-butyl ether. The organic phase is dried over sodium sulfate. After the solvent has been stripped off, the crude product is chromatographed over a silica gel column (mobile phase: 9:1 toluene/ethyl acetate). 3.1 g of the title compound are obtained as colorless crystals of melting point 132°–148° C.

$^1$H-NMR (CDCl$_3$, δ in ppm): 2.4 (s, 3H); 3.7 (s, 3H); 3.8 (s, 3H); 6.85 (d, 2H); 7.1–7.75 (m, 10H); 7.8 (s, 1H)

PREPARATION EXAMPLE 2

Preparation of methyl
α-2-[2-(4-chloro-3-phenylisoxazol-5-yl)-ethen-1-yl]-phenyl-β-methoxyacrylate (Example No. 3.17)

A solution of 6.6 g of methyl 4-chloro-3-phenylisoxazol-5-ylmethanephosphonate in 50 ml of dimethylformamide is added dropwise to a suspension of 0.53 g of sodium hydride in 20 ml of anhydrous dimethylformamide at room temperature. Stirring is continued for a further ... minutes, and a solution of 4.4 g of 2-(β-methoxy-α-methoxycarbonylvinyl)-benzaldehyde in 50 ml of dimethylformamide is metered into the dark brown mixture in the course of 60 minutes. After a further 3 hours, the mixture is hydrolyzed with ice water and extracted with methyl tert-butyl ether. The organic phase is dried over sodium sulfate. After the solvent has been stripped off, a solid remains. Trituration with a little methyl tertbutyl ether gives 4.0 g of the title compound as colorless crystals of melting point 129°–136° C.

$^1$H-NMR (CDCl$_3$, δ in ppm): 3.75 (s, 3H); 3.85 (s, 3H); 7.0 (d, 1H); 7.2–7.9 (m, 11H)

PREPARATION EXAMPLE 3

Preparation of methyl
α-2-(2-[4-ethyl-5-(4-chlorophenyl)isoxazol-3-yl]-ethen-1-yl)-⊖-methoxyacrylate (Example No. 4.23)

A solution of 6.2 g of diethyl 4-ethyl-5-(4-chlorophenyl)-isoxazol-3-ylmethanephosphonate in 20 ml of dimethylformamide is added dropwise to a suspension of 0.53 g of sodium hydride in 20 ml of anhydrous dimethylformamide at room temperature. Stirring is continued for a further 20 minutes, and a solution of 4.4 g of 2-(β-methoxy-α-methoxycarbonylvinyl)-benzaldehyde in 20 ml of dimethylformamide is metered into the dark brown mixture in the course of 60 minutes. After a further 3 hours, the mixture is hydrolyzed with ice water and extracted with methyl tert-butyl ether. The organic phase is dried over sodium sulfate. After the solvent has been stripped off, the crude product is chromatographed over a silica gel column (mobile phase:toluene). 2.6 g of the title compound are obtained as crystals of melting point 117°–120° C.

$^1$H-NMR (CDCl$_3$, δ in ppm): 1.25 (t, 3H); 2.7 (q, 2H); 3.7 (s, 3H); 3.85 (s, 3H); 6.95 (d, 1H); 7.1–7.8 (m, 10H)

TABLE 1

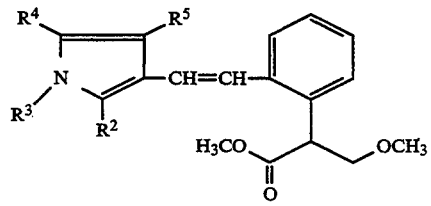

| No. | $R^2$ | $R^3$ | $R^4$ | $R^5$ |
|---|---|---|---|---|
| 1.01 | H | CH$_3$ | CH$_3$ | H |
| 1.02 | H | CH(CH$_3$)$_2$ | CH$_3$ | H |
| 1.03 | H | C(CH$_3$)$_3$ | CH$_3$ | H |
| 1.04 | H | C$_6$H$_5$ | CH$_3$ | H |
| 1.05 | CH$_3$ | CH$_3$ | H | H |
| 1.06 | CH$_3$ | CH(CH$_3$)$_2$ | H | H |
| 1.07 | CH$_3$ | C(CH$_3$)$_3$ | H | H |
| 1.08 | CH$_3$ | C$_6$H$_5$ | H | H |

TABLE 1-continued

Structure: Pyrazole with R³ on N, R² and R⁴, R⁵ substituents; CH=CH linker to phenyl with H₃CO-C(=O)- and -OCH₃ groups.

| No. | R² | R³ | R⁴ | R⁵ |
|---|---|---|---|---|
| 1.09 | $CH_3$ | 4-F—$C_6H_4$ | H | H |
| 1.10 | $CO_2CH_3$ | $CH_3$ | H | H |
| 1.11 | $CO_2CH_3$ | $CH(CH_3)_2$ | H | H |
| 1.12 | $CO_2CH_3$ | $C_6H_5$ | H | H |
| 1.13 | $CO_2CH_3$ | 4-F—$C_6H_4$ | H | H |
| 1.14 | Cl | $CH_3$ | H | H |
| 1.15 | Cl | $CH(CH_3)_2$ | H | H |
| 1.16 | Cl | $C(CH_3)_3$ | H | H |
| 1.17 | Cl | $C_6H_5$ | H | H |
| 1.18 | Cl | 4-Cl—$C_6H_4$ | H | H |
| 1.19 | Cl | 3-Cl—$C_6H_4$ | H | H |
| 1.20 | Cl | 4-Br—$C_6H_4$ | H | H |
| 1.21 | Cl | 3-Br—$C_6H_4$ | H | H |
| 1.22 | H | $C_6H_5$ | H | CN |

TABLE 2

| No. | R² | R³ | R⁵ | mp or IR value |
|---|---|---|---|---|
| 2.01 | H | $CH_3$ | $CH_3$ | |
| 2.02 | H | $CH(CH_3)_2$ | $CH_3$ | |
| 2.03 | H | $C(CH_3)_3$ | $CH_3$ | |
| 2.04 | H | $C_6H_5$ | $CH_3$ | |
| 2.05 | H | 4-$CH_3$—$C_6H_4$ | $CH_3$ | |
| 2.06 | H | 4-Cl—$C_6H_4$ | $CH_3$ | 146–150° C. |
| 2.07 | H | 3-Cl—$C_6H_4$ | $CH_3$ | |
| 2.08 | H | 4-F—$C_6H_4$ | $CH_3$ | |
| 2.09 | H | 2,6-di-F—$C_6H_3$ | $CH_3$ | |
| 2.10 | H | 4-$OCH_3$—$C_6H_4$ | $CH_3$ | |
| 2.11 | $CH_3$ | $C_6H_5$ | $CH_3$ | |
| 2.12 | $CH_3$ | 4-$CH_3$—$C_6H_4$ | $CH_3$ | |
| 2.13 | $CH_3$ | 4-Cl—$C_6H_4$ | $CH_3$ | 159–164° C. |
| 2.14 | $CH_3$ | 3-Cl—$C_6H_4$ | $CH_3$ | |
| 2.15 | $CH_3$ | 4-F—$C_6H_4$ | $CH_3$ | |
| 2.16 | $CH_3$ | 3-F—$C_6H_3$ | $CH_3$ | |
| 2.17 | $C_2H_5$ | $C_6H_5$ | H | |
| 2.18 | $CH_3$ | $C_6H_5$ | H | 132–148° C. |
| 2.19 | $CH_3$ | 4-Cl—$C_6H_4$ | H | 128–134° C. |
| 2.20 | $CH_3$ | 4-$CH_3$—$C_6H_4$ | H | |
| 2.21 | Cl | $CH(CH_3)_2$ | H | |
| 2.22 | Cl | $C(CH_3)_3$ | H | |
| 2.23 | Cl | $C_6H_5$ | H | |
| 2.24 | Cl | 4-Me—$C_6H_4$ | H | |
| 2.25 | Cl | 3-Me—$C_6H_4$ | H | |
| 2.26 | Cl | 4-Cl—$C_6H_4$ | H | |
| 2.27 | Cl | 3-Cl—$C_6H_4$ | H | |
| 2.28 | Cl | 2,6-diCl—$C_6H_3$ | H | |
| 2.29 | Cl | 3,4-diCl—$C_6H_3$ | H | |
| 2.30 | Cl | 4-F—$C_6H_4$ | H | |
| 2.31 | Cl | 3-F—$C_6H_4$ | H | |
| 2.32 | Cl | 2,6-diF—$C_6H_3$ | H | |
| 2.33 | Cl | $C_6H_5$ | $CH_3$ | |
| 2.34 | Cl | 4-Me—$C_6H_4$ | $CH_3$ | |
| 2.35 | Cl | 3-Me—$C_6H_4$ | $CH_3$ | |
| 2.36 | Cl | 4-Cl—$C_6H_4$ | $CH_3$ | |
| 2.37 | Cl | 3-Cl—$C_6H_4$ | $CH_3$ | |
| 2.38 | Cl | 2,4-di-Cl—$C_6H_3$ | $CH_3$ | |
| 2.39 | Cl | 3,5-di-Cl—$C_6H_3$ | $CH_3$ | |
| 2.40 | Cl | 4-F—$C_6H_4$ | $CH_3$ | |
| 2.41 | Cl | 3-F—$C_6H_4$ | $CH_3$ | |
| 2.42 | Cl | 2,4-diF—$C_6H_3$ | $CH_3$ | |
| 2.43 | Cl | 2,6-diF—$C_6H_3$ | $CH_3$ | |
| 2.44 | Cl | 3,4-diF—$C_6H_3$ | $CH_3$ | |
| 2.45 | $CO_2CH_3$ | $CH(CH_3)_2$ | H | |
| 2.46 | $CO_2CH_3$ | $C(CH_3)_3$ | H | |
| 2.47 | $CO_2CH_3$ | $C_6H_5$ | H | |
| 2.48 | $CO_2CH_3$ | 4-Cl—$C_6H_4$ | H | |
| 2.49 | $CO_2CH_3$ | 4-Me—$C_6H_4$ | H | |
| 2.50 | $CO_2CH_3$ | 4-F—$C_6H_4$ | H | |
| 2.51 | $CF_3$ | $CH(CH_3)_3$ | H | |
| 2.52 | $CF_3$ | $C(CH_3)_3$ | H | |
| 2.53 | $CF_3$ | $C_6H_5$ | H | 165–168° C. |
| 2.54 | $CF_3$ | 4-Cl—$C_6H_4$ | H | 157–163° C. |
| 2.55 | $CF_3$ | 3-Cl—$C_6H_4$ | H | 135–137° C. |
| 2.56 | $CF_3$ | 4-F—$C_6H_4$ | H | 145–150° C. |
| 2.57 | $CF_3$ | 4-Me—$C_6H_4$ | H | 177–180° C. |
| 2.58 | $CF_3$ | 4-MeO—$C_6H_4$ | H | 134–137° C. |
| 2.59 | $CF_3$ | 2,4-di-Cl—$C_6H_3$ | H | 141–144° C. |

TABLE 3

| No. | R² | R³ | mp or IR value |
|---|---|---|---|
| 3.01 | $CO_2CH_3$ | $CH_3$ | |
| 3.02 | $CO_2CH_3$ | $CH(CH_3)_2$ | |
| 3.03 | $CO_2CH_3$ | $C(CH_3)_3$ | |
| 3.04 | $CO_2CH_3$ | $C_6H_5$ | |
| 3.05 | $CO_2CH_3$ | 4-Cl—$C_6H_4$ | |
| 3.06 | $CO_2CH_3$ | 3-F—$C_6H_4$ | |
| 3.07 | $CO_2CH_3$ | 2,3-diF—$C_6H_3$ | |
| 3.08 | $CO_2CH_3$ | 4-$CH_3$—$C_6H_4$ | |
| 3.09 | $CH_3$ | $CH(CH_3)_2$ | |
| 3.10 | $CH_3$ | $C_6H_5$ | |
| 3.11 | Cl | $CH_3$ | |
| 3.12 | Cl | $C_2H_5$ | |
| 3.13 | Cl | $CH(CH_3)_2$ | 2973, 1711, 1633, 1258, 1129 cm⁻¹ |
| 3.14 | Cl | $C(CH_3)_3$ | |
| 3.15 | Cl | $CH_2OCH_3$ | |
| 3.16 | Cl | 2-Tetrahydrofuranyl | 114–119° C. |
| 3.17 | Cl | $C_6H_5$ | 129–136° C. |
| 3.18 | Cl | 4-Me—$C_6H_4$ | 136° C. |
| 3.19 | Cl | 3-Me—$C_6H_4$ | 106–107° C. |
| 3.20 | Cl | 2-Me—$C_6H_4$ | |
| 3.21 | Cl | 3,4-diMe—$C_6H_3$ | |
| 3.22 | Cl | 3,5-diMe—$C_6H_3$ | |
| 3.23 | Cl | 4-F—$C_6H_4$ | 148–150° C. |
| 3.24 | Cl | 3-F—$C_6H_4$ | 134–135° C. |
| 3.25 | Cl | 2-F—$C_6H_4$ | |
| 3.26 | Cl | 3,4-diF—$C_6H_3$ | 151–152° C. |
| 3.27 | Cl | 2,4-diF—$C_6H_3$ | |
| 3.28 | Cl | 3,5-diF—$C_6H_3$ | |
| 3.29 | Cl | 2,6-diF—$C_6H_3$ | 1708, 1633, 1472, 1258, 1129, 1008 cm⁻¹ |
| 3.30 | Cl | 2,5-diF—$C_6H_3$ | |
| 3.31 | Cl | 4-Cl—$C_6H_3$ | 150–151° C. |
| 3.32 | Cl | 3-Cl—$C_6H_3$ | 157–159° C. |
| 3.33 | Cl | 2-Cl—$C_6H_3$ | 1707, 1639, 1284, |

TABLE 3-continued

Structure: R³ and R² on isoxazole ring (N—O), connected via CH=CH to phenyl bearing C(=O)OCH₃ and =CH—OCH₃ substituents.

| No. | R² | R³ | mp or IR value |
|---|---|---|---|
| | | | 1258, 1131 cm⁻¹ |
| 3.34 | Cl | 3,4-diCl—C₆H₃ | |
| 3.35 | Cl | 2,4-diCl—C₆H₃ | |
| 3.36 | Cl | 3,5-diCl—C₆H₃ | 191–193° C. |
| 3.37 | Cl | 2,6-diCl—C₆H₃ | |
| 3.38 | Cl | 2,5-diCl—C₆H₃ | |
| 3.39 | Cl | 4-Br—C₆H₄ | |
| 3.40 | Cl | 3-Br—C₆H₄ | |
| 3.41 | Cl | 3,5-diBr—C₆H₃ | |
| 3.42 | Cl | 2,4-diBr—C₆H₃ | |
| 3.43 | Cl | 2,6-diBr—C₆H₃ | |
| 3.44 | Cl | 4-C₆H₅—C₆H₄ | |
| 3.45 | Cl | 3-C₆H₅—C₆H₄ | |
| 3.46 | Cl | 4-NO₂—C₆H₄ | |
| 3.47 | Cl | 3-NO₂—C₆H₄ | |
| 3.48 | Cl | 4-CH₃O—C₆H₄ | |
| 3.49 | Cl | 3-CH₃O—C₆H₄ | |
| 3.50 | Cl | 4-CN—C₆H₄ | |
| 3.51 | Cl | 3-CN—C₆H₄ | |
| 3.52 | Cl | 4-CF₃ | 113–117° C. |
| 3.53 | Cl | 3-CF₃ | 163–167° C. |
| 3.54 | Cl | Pyrid-2-yl | |
| 3.55 | Cl | Pyrid-3-yl | |
| 3.56 | Cl | Pyrid-4-yl | |
| 3.57 | Cl | 6-CH₃-Pyrid-2-yl | |
| 3.58 | Cl | cyclo-C₃H₅ | |
| 3.59 | Cl | cyclo-C₅H₉ | |
| 3.60 | Cl | cyclo-C₆H₁₁ | |
| 3.61 | Cl | 4-Cl-3-[CH(CH₃)₂]-isoxazol-5-yl | |
| 3.62 | Cl | 4-Cl-3-CH₃-isoxazol-5-yl | |
| 3.63 | Br | CH(CH₃)₂ | |
| 3.64 | Br | C(CH₃)₃ | |
| 3.65 | Br | C₆H₅ | |
| 3.66 | Br | 4-F—C₆H₄ | |
| 3.67 | Br | 3-F—C₆H₄ | |
| 3.68 | Br | 4-Cl—C₆H₄ | |
| 3.69 | Br | 3-Cl—C₆H₄ | |
| 3.70 | Br | 4-CH₃—C₆H₄ | |
| 3.71 | Br | 3-CH₃—C₆H₄ | |

TABLE 4

Structure: R³ and R² on isoxazole ring (O—N), connected via CH=CH to phenyl bearing C(=O)OCH₃ and =CH—OCH₃ substituents.

| No. | R² | R³ | mp or IR value |
|---|---|---|---|
| 4.01 | CO₂CH₃ | CH₃ | |
| 4.02 | CO₂CH₃ | CH(CH₃)₂ | |
| 4.03 | CO₂CH₃ | C(CH₃)₃ | |
| 4.04 | CO₂CH₃ | C₆H₅ | |
| 4.05 | CO₂CH₃ | 4-Cl—C₆H₄ | |
| 4.06 | CO₂CH₃ | 3-F—C₆H₄ | |
| 4.07 | CO₂CH₃ | 2,3-diF—C₆H₃ | |
| 4.08 | CO₂CH₃ | 4-CH₃—C₆H₄ | |
| 4.09 | CH₃ | CH(CH₃)₂ | |
| 4.10 | CH₃ | C₆H₅ | |
| 4.11 | CH₃ | 4-F—C₆H₄ | |
| 4.12 | CH₃ | 3-F—C₆H₄ | |
| 4.13 | CH₃ | 4-Cl—C₆H₄ | 121–123° C. |
| 4.14 | CF₃ | 3-Cl—C₆H₄ | 148–150° C. |
| 4.15 | CF₃ | 2,4-diCl—C₆H₃ | |
| 4.16 | CF₃ | 2,6-diCl—C₆H₃ | |
| 4.17 | CF₃ | 3,5-diCl—C₆H₃ | |
| 4.18 | CF₃ | 4-CH₃—C₆H₄ | |
| 4.19 | CF₃ | 3-CH₃—C₆H₄ | |
| 4.20 | CF₃ | 4-CF₃—C₆H₄ | |
| 4.21 | CF₃ | 3-CF₃—C₆H₄ | |
| 4.22 | C₂H₅ | C₆H₅ | 119° C. |
| 4.23 | C₂H₅ | 4-Cl—C₆H₄ | 117–120° C. |
| 4.24 | C₂H₅ | 3-Cl—C₆H₄ | |
| 4.25 | C₂H₅ | 3,5-diF—C₆H₃ | |
| 4.26 | Cl | CH₃ | |
| 4.27 | Cl | C₂H₅ | |
| 4.28 | Cl | CH(CH₃)₂ | |
| 4.29 | Cl | C(CH₃)₃ | |
| 4.30 | Cl | CH₂OCH₃ | |
| 4.31 | Cl | 2-Tetrahydrofuranyl | |
| 4.32 | Cl | C₆H₅ | |
| 4.33 | Cl | 4-Me—C₆H₄ | |
| 4.34 | Cl | 3-Me—C₆H₄ | |
| 4.35 | Cl | 2-Me—C₆H₄ | |
| 4.36 | Cl | 3,4-diMe—C₆H₃ | |
| 4.37 | Cl | 3,5-diMe—C₆H₃ | |
| 4.38 | Cl | 4-F—C₆H₄ | |
| 4.39 | Cl | 3-F—C₆H₄ | |
| 4.40 | Cl | 2-F—C₆H₄ | |
| 4.41 | Cl | 3,4-diF—C₆H₃ | |
| 4.42 | Cl | 2,4-diF—C₆H₃ | |
| 4.43 | Cl | 3,5-diF—C₆H₃ | |
| 4.44 | Cl | 2,6-diF—C₆H₃ | |
| 4.45 | Cl | 2,5-diF—C₆H₃ | |
| 4.46 | Cl | 4-Cl—C₆H₃ | |
| 4.47 | Cl | 3-Cl—C₆H₃ | |
| 4.48 | Cl | 2-Cl—C₆H₃ | |
| 4.49 | Cl | 3,4-diCl—C₆H₃ | |
| 4.50 | Cl | 2,4-diCl—C₆H₃ | |
| 4.51 | Cl | 3,5-diCl—C₆H₃ | |
| 4.52 | Cl | 2,6-diCl—C₆H₃ | |
| 4.53 | Cl | 2,5-diCl—C₆H₃ | |
| 4.54 | Cl | 4-Br—C₆H₄ | |
| 4.55 | Cl | 3-Br—C₆H₄ | |
| 4.56 | Cl | 3,5-diBr—C₆H₃ | |
| 4.57 | Cl | 2,4-diBr—C₆H₃ | |
| 4.58 | Cl | 2,6-diBr—C₆H₃ | |
| 4.59 | Cl | 4-C₆H₅—C₆H₄ | |
| 4.60 | Cl | 3-C₆H₅—C₆H₄ | |
| 4.61 | Cl | 4-NO₂—C₆H₄ | |
| 4.62 | Cl | 3-NO₂—C₆H₄ | |
| 4.63 | Cl | 4-CH₃O—C₆H₄ | |
| 4.64 | Cl | 3-CH₃O—C₆H₄ | |
| 4.65 | Cl | 4-CN—C₆H₄ | |
| 4.66 | Cl | 3-CN—C₆H₄ | |
| 4.67 | Cl | 4-CF₃—C₆H₄ | |
| 4.68 | Cl | 3-CF₃—C₆H₄ | |
| 4.69 | Cl | Pyrid-2-yl | |
| 4.70 | Cl | Pyrid-3-yl | |
| 4.71 | Cl | Pyrid-4-yl | |
| 4.72 | Cl | 6-CH₃-Pyrid-2-yl | |
| 4.73 | Cl | cyclo-C₃H₅ | |
| 4.74 | Cl | cyclo-C₅H₉ | |
| 4.75 | Cl | cyclo-C₆H₁₁ | |
| 4.76 | Br | CH(CH₃)₂ | |
| 4.77 | Br | C(CH₃)₂ | |
| 4.78 | Br | C₆H₅ | |
| 4.79 | Br | 4-F—C₆H₄ | |
| 4.80 | Br | 3-F—C₆H₄ | |
| 4.81 | Br | 4-Cl—C₆H₄ | |

TABLE 4-continued
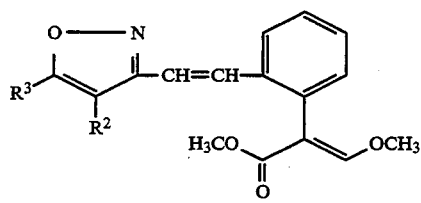
| No. | R² | R³ | mp or IR value |
|---|---|---|---|
| 4.82 | Br | 3-Cl—C₆H₄ | |
| 4.83 | Br | 4-CH₃—C₆H₄ | |
| 4.84 | Br | 3-CH₃—C₆H₄ | |
TABLE 5
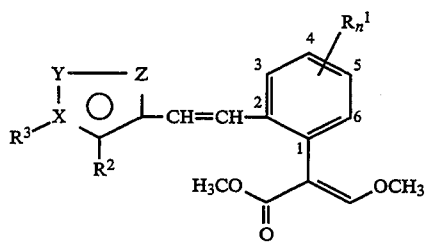
| No. | $R_n^1$ | 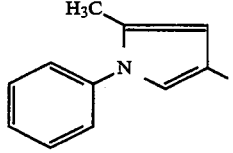 (structure) | mp or IR value |
|---|---|---|---|
| 5.01 | 3-Cl | 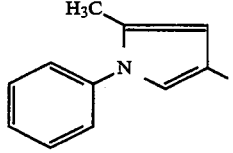 | |
| 5.02 | 3-Cl | 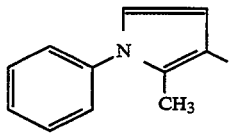 | |
| 5.03 | 3-Cl | 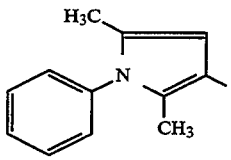 | |
| 5.04 | 4-Cl | 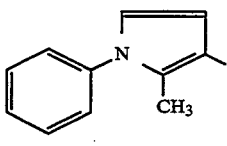 | |
| 5.05 | 6-Cl | 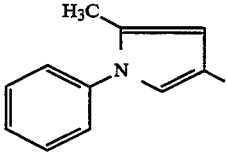 | |
| 5.06 | 4-OCH₃ | 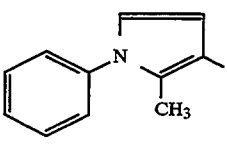 | |

TABLE 5-continued
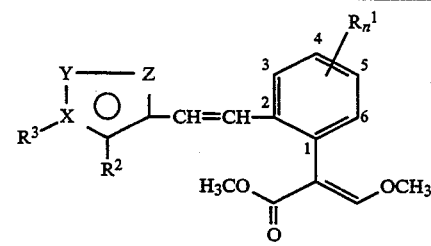
| No. | $R_n^1$ | | mp or IR value |
|---|---|---|---|
| 5.07 | 4-OCH$_3$ | 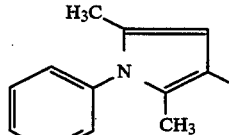 | |
| 5.08 | 4-C(CH$_3$)$_3$ | 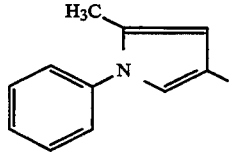 | |
| 5.09 | 6-CH$_3$ | 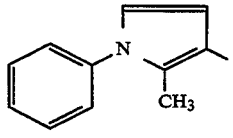 | |
| 5.10 | 6-CH$_3$ | 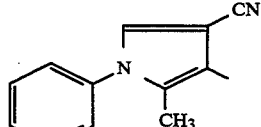 | |
| 5.11 | 3-Cl | 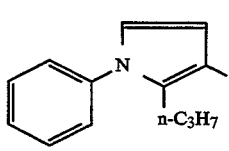 | |
| 5.12 | 6-CH$_3$ | 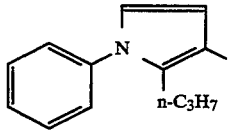 | |
| 5.13 | 3-Cl | 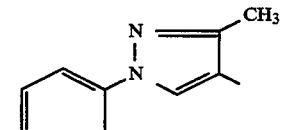 | |
| 5.14 | 3-Cl | 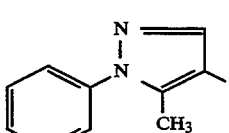 | |

TABLE 5-continued

| No. | $R_n^1$ | (substituent group) | mp or IR value |
|---|---|---|---|
| 5.15 | 4-Cl | 1-phenyl-5-methylpyrazol-3-yl (with 4-CH3) | |
| 5.16 | 4-OCH3 | 1-phenyl-3,4,5-trimethylpyrazol-? | |
| 5.17 | 4-C(CH3)3 | 1-phenyl-4,5-dimethylpyrazol-3-yl | |
| 5.18 | 6-Cl | 1-phenyl-3,4-dimethylpyrazol-5-yl | |
| 5.19 | 6-CH3 | 1-phenyl-3,4-dimethylpyrazol-5-yl | |
| 5.20 | H | 2-(4,6-dimethylpyrimidin-2-yl)-4-n-propylpyrazol-3-yl | |
| 5.21 | H | 2-(pyridin-2-yl)-4-n-propylpyrazol-3-yl | |

TABLE 5-continued
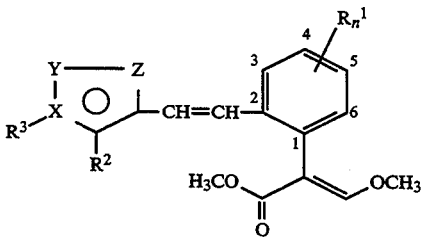
| No. | $R_n^1$ | | mp or IR value |
|---|---|---|---|
| 5.22 | 6-Cl | 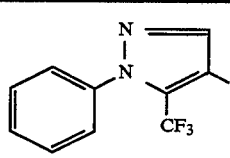 | |
| 5.23 | 4-C(CH$_3$)$_2$ | 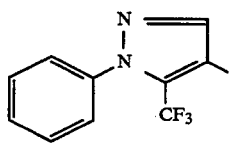 | |
| 5.24 | H | 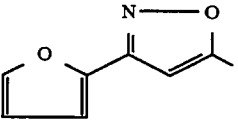 | 1707, 1631, 1445, 1254, 1131 cm$^{-1}$ |
| 5.25 | H | 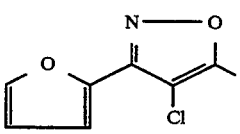 | |
| 5.25 | H | 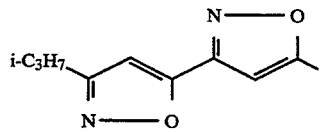 | 135–138° C. |
| 5.26 | H | 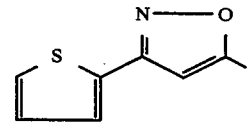 | 2938, 1695, 1620, 1257, 1126 cm$^{-1}$ |
| 5.27 | 4-C(CH$_3$)$_3$ | 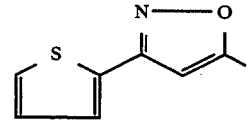 | |
| 5.28 | 6-Cl | 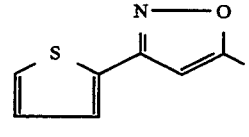 | |

TABLE 5-continued

| No. | $R_n^1$ | structure | mp or IR value |
|---|---|---|---|
| 5.29 | H | (trichlorothiophene-isoxazole with Cl) | |
| 5.30 | H | (N-methylpyrazole-isoxazole) | 2940, 1707, 1634, 1257, 1129 cm$^{-1}$ |
| 5.31 | 4-CH$_3$O | (N-methylpyrazole-isoxazole) | |
| 5.32 | 6-Cl | (N-methylpyrazole-isoxazole) | |
| 5.33 | H | (phenyl-isothiazole, n-C$_3$H$_7$) | |
| 5.34 | H | (4-chlorophenyl-isothiazole, n-C$_3$H$_7$) | |
| 5.35 | H | (3-chlorophenyl-isothiazole, Cl) | |

TABLE 5-continued

[Structure: generic formula with substituted phenyl bearing Rn¹ at positions 3,4,5,6, CH=CH linkage, and H₃CO-C(=O)-C=CH-OCH₃ group, with side ring system containing X, Y, Z, R², R³]

| No. | Rn¹ | (substituent structure) | mp or IR value |
|---|---|---|---|
| 5.36 | H | N=S isothiazole with CH₃, linked via N to chain with CH₃ groups | |
| 5.37 | 3-Cl | 3-(4-chlorophenyl)-5-methylisothiazole | |
| 5.38 | 4-C(CH₃)₃ | 3-(4-chlorophenyl)-5-methylisothiazole | |
| 5.39 | 3-Cl | N-phenylpyrrole with methyl | |
| 5.40 | 4-Cl | N-phenylpyrrole with methyl | |
| 5.41 | 6-Cl | N-phenylpyrrole with methyl | |
| 5.42 | 4-F | N-phenylpyrrole with methyl | |
| 5.43 | 4-OMe | N-phenylpyrrole with methyl | |

TABLE 5-continued

| No. | $R_n^1$ | (structure) | mp or IR value |
|---|---|---|---|
| 5.44 | 6-OMe | N-phenylpyrrole | |
| 5.45 | 4-C(CH$_3$)$_3$ | N-phenylpyrrole | |
| 5.46 | 5-C(CH$_3$)$_3$ | N-phenylpyrrole | |
| 5.47 | 6-CH$_3$ | N-phenylpyrrole | |
| 5.48 | 3-Cl | N-phenylpyrazole | |
| 5.49 | 4-Cl | N-phenylpyrazole | |
| 5.50 | 6-Cl | N-phenylpyrazole | |
| 5.51 | 4-F | N-phenylpyrazole | |

TABLE 5-continued

| No. | $R_n^1$ | [substituent structure] | mp or IR value |
|---|---|---|---|
| 5.52 | 4-OMe | 1-phenyl-pyrazol-5-yl | |
| 5.53 | 6-OMe | 1-phenyl-pyrazol-5-yl | |
| 5.54 | 4-C(CH₃)₃ | 1-phenyl-pyrazol-5-yl | |
| 5.55 | 5-C(CH₃)₃ | 1-phenyl-pyrazol-5-yl | |
| 5.56 | 6-CH₃ | 1-phenyl-pyrazol-5-yl | |
| 5.57 | 3-Cl | 3-phenyl-isoxazol-5-yl | |
| 5.58 | 4-Cl | 3-phenyl-isoxazol-5-yl | |
| 5.59 | 6-Cl | 3-phenyl-isoxazol-5-yl | |

TABLE 5-continued

| No. | $R_n^1$ | (substituent structure) | mp or IR value |
|---|---|---|---|
| 5.60 | 4-F | 3-phenyl-5-methylisoxazole | |
| 5.61 | 4-OMe | 3-phenyl-5-methylisoxazole | |
| 5.62 | 6-OMe | 3-phenyl-5-methylisoxazole | |
| 5.63 | 4-C(CH$_3$)$_3$ | 3-phenyl-5-methylisoxazole | |
| 5.64 | 5-C(CH$_3$)$_3$ | 3-phenyl-5-methylisoxazole | |
| 5.65 | 6-CH$_3$ | 3-phenyl-5-methylisoxazole | |
| 5.66 | 3-Cl | 5-phenyl-3-methylisoxazole | |
| 5.67 | 4-Cl | 5-phenyl-3-methylisoxazole | |

TABLE 5-continued

| No. | $R_n^1$ | (structure) | mp or IR value |
|---|---|---|---|
| 5.68 | 6-Cl | 5-phenyl-3-methyl-isoxazole | |
| 5.69 | 4-F | 5-phenyl-3-methyl-isoxazole | |
| 5.70 | 4-OMe | 5-phenyl-3-methyl-isoxazole | |
| 5.71 | 6-OMe | 5-phenyl-3-methyl-isoxazole | |
| 5.72 | 4-C(CH$_3$)$_3$ | 5-phenyl-3-methyl-isoxazole | |
| 5.73 | 5-C(CH$_3$)$_3$ | 5-phenyl-3-methyl-isoxazole | |
| 5.74 | 6-CH$_3$ | 5-phenyl-3-methyl-isoxazole | |
| 5.75 | H | bis-isoxazole structure | 147–154° C. |

TABLE 5-continued

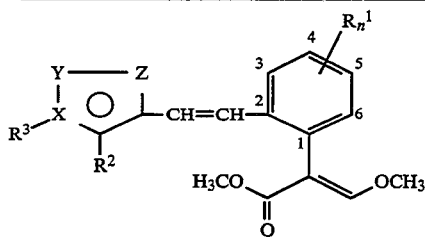

| No. | $R_n^1$ | | mp or IR value |
|---|---|---|---|
| 5.76 | 4-OMe | 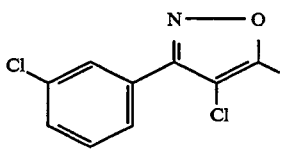 | 160–163° C. |
| 5.77 | 4-OMe | 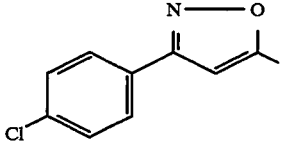 | 138–143° C. |
| 5.78 | 4-C(CH₃)₃ | 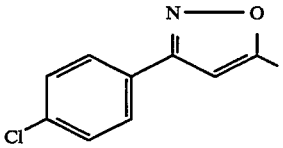 | 185–190° C. |
| 5.79 | 4-Cl | 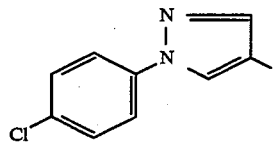 | 176–179° C. |
| 5.80 | 4-Cl | 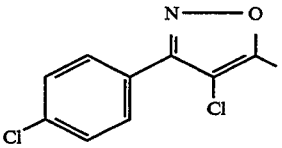 | 178–182° C. |

The novel compounds are suitable for use as fungicides.

The novel compounds I, or the agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Normally, the plants are sprayed or dusted with the active ingredients, or the seeds of the plants are treated with them.

The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Examples of such formulations are given below.

I. A solution of 90 parts by weight of compound no. 1 and 10 parts by weight of N-methyl-α-pyrrolidone, which is suitable for application in the form of very fine drops.

II. A mixture of 20 parts by weight of compound no. 1, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 1, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound no. 1, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

V. A hammer-milled mixture of 80 parts by weight of compound no. 1, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 1 and 97 parts by weight of particulate kaolin. The dust contains 3 wt % of the active ingredient.

VII. An intimate mixture of 30 parts by weight of compound no. 1, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 1, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 1, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

The novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The compounds are applied by treating the fungi, or the seeds, plants, materials or soil to be protected against fungus attack with a fungicidally effective amount of the active ingredients.

The active ingredients may be applied before or after infection of the materials, plants or seeds by the fungi.

Specifically, the compounds I are useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
*Puccinia* species in cereals,
*Rhizoctonia solani* in cotton,
*Ustilago* species in cereals and sugar cane,
*Venturia inaequalis* (scab) in apples,
*Helminthosporium* species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
*Fusarium* and *Verticillium* species in various plants,
*Plasmopara viticola* in grapes,
*Alternaria* species in fruit and vegetables.

The novel compounds may also be used for protecting materials (timber), e.g., against *Paecilomyces variotii*.

The fungicidal agents generally contain from 0.1 to 95, and preferably from 0.5 to 90, wt % of active ingredient.

The application rates depend on the type of effect desired, and vary from 0.02 to 3 kg of active ingredient per hectare.

When the active ingredients are used for treating seed, rates of from 0.001 to 50, and preferably from 0.01 to 10, g are generally required per kg of seed.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater spectrum of fungicidal action.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-b)s-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylth)o)-tetrahydrophthalimide,
N-trichloromethylthiotetrahydrophthalimide,
N-trichloromethylth)ophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
4-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethyphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichiorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

The compounds of the formula I are suitable for effectively combating pests such as insects, arachnids and nematodes. They may be used as pesticides in crop protection and in the hygiene, stores protection and veterinary sectors.

Examples of injurious insects belonging to the Lepidoptera order are *Agrotis ypsilon, Agrotis segetum, Alabama argillacea, Anticarsia gemmatalis, Argyresthia conjugella, Autographa gamma, Bupalus piniarius, Cacoecia* murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis.

Examples from the Coleoptera order are *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, LimoniuS californicus, Lissorhoptrus oryzophilus, Melanotus communis, Meligethes aeneus, Melolontha hippocastani, Melolontha melolontha, Onlema oryzae, Ortiorrhynchus sulcatus, Ortiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria.*

Examples from the Diptera order are *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa.*

Examples from the Thysanoptera order are *Frankliniella fusca, Frankliniella occidentalis, Frankliniella tritici, Scirtothrips citri, Thrips oryzae, Thrips palmi* and *Thrips tabaci.*

Examples from the Hymenoptera order are *Athalia rosae, Atta cephalotes, Atta sexdens, Alta texana, Hoplocampa minuta, Hoplocampa testudinea, Monomorium pharaonis, Solenopsis geminata* and Solenopsis invicta.

Examples from the Heteroptera order are *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor.*

Examples from the Homoptera order are *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii.*

Examples from the Isoptera order are *Calotermes flavicollis, Leucotermes flavipes, Reticulitermes lucifugus* and *Termes natalensis.*

Examples from the Orthoptera order are *Acheta domestica, Blatta orientalis, Blattella germanica, Forficula auricularia, Gryllotalpa gryllotalpa, Locusta migratoria, Melanoplus birittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus.*

Examples from the Acarina order are *Amblyomma americahum, Amglyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius* and *Tetranychus urticae.*

Examples from the nematodes class are root-knot nematodes, e.g., *Meloidogyne hapla, Meloidogyne incognita* and *Meloidogyne javanica,* cyst-forming nematodes, e.g., *Globodera rostochiensis, Heterodera avenae, Hetrodera glycinae, Heterodera schachtii* and *Heterodera trifolii,* and stem and leaf eelworms, e.g., *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The active ingredient concentrations in the finished formulations may vary over a wide range; generally, they are from 0.0001 to 10, and preferably from 0.01 to 1, %.

The active ingredients may also successfully be used in the ultra-low-volume method (ULV), in which it is possible to apply formulations containing more than 95 wt % of the active ingredient, or even the active ingredient without any additives at all.

When the active ingredients are used for combating pests in the open, the application rates are from 0.1 to 2.0, and preferably from 0.2 to 1.0, kg/ha.

USE EXAMPLES

For comparison purposes, compounds nos. 121 (A), 279 (B), 147 (C), 123 (D) and 125 (E) disclosed in EP 378 755 were used.

USE EXAMPLE 1

Action On Wheat Brown Rust

Leaves of pot-grown wheat seedlings of the "Frühgold" variety were dusted with spores of brown rust (*Puccinia recondita*). The pots were then placed for 24 hours at 20° to 22° C. in a high-humidity (90-95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that compounds nos. 3.13, 3.17, 4.22, 4.23 and 3.23, applied as aqueous spray liquors containing 250 ppm of active ingredient, have a better fungicidal action (90%) than prior art comparative agents A, B and C (60%).

USE EXAMPLE 2

Action on *Septoria nodorum*

Leaves of pot-grown wheat seedlings of the "Jubilar" variety were sprayed to runoff with aqueous spray liquors consisting (dry basis) of 80% of active ingredient and 20% of emulsifier. The next day the plants were inoculated with an aqueous spore suspension of Septoria nodorum, and cultivated for a week at from 17° to 19° C. and a relative humidity of 95%. The spread of the symptoms was then assessed visually.

The results show that compounds nos. 3.31, 3.17 and 3.18, applied as aqueous spray liquors containing 500 ppm of active ingredient, have a better fungicidal action (95%) than prior art agents D, B and E (60%).

We claim:

1. An α-arylacrylic acid derivative of the formula I

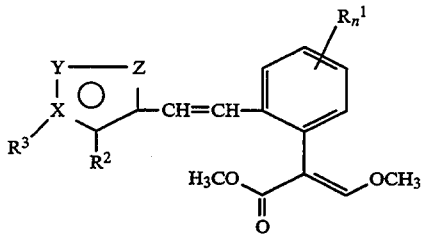

where
(a) X is C, Y is O, and Z is N; or
(b) X is C, Y is N, and Z is O; or
(c) X is N, Y is N, and Z is $CR^4$;
n is from 0 to 4
$R^1$ is nitro, cyano, halogen;
$C_1$-$C_4$-alkyl, $C_1$-$C_4$-alkoxy, partially or completely halogenated $C_1$-$C_4$-alkyl, partially or completely halogenated $C_1$-$C_4$-alkoxy or $C_1$-$C_4$-alkylthio,
or, where n is 2, 3 or 4, two adjacent substituents $R^1$ together form 1,3-butadiene-1,4-diyl, which may carry from one to four halogen atoms and/or one or two of the following groups: nitro, cyano, $C_1$-$C_4$-alkyl, $C_1$-$C_4$-alkoxy, partially or completely halogenated $C_1$-$C_4$-alkyl, partially or completely halogenated $C_1$-$C_4$-alkoxy or $C_1$-$C_4$-alkylthio;
$R^2$ is $C_1$-$C_4$-alkyl, partially or completely halogenated $C_1$-$C_4$-alkyl, halogen, cyano, nitro, $C_1$-$C_4$-alkoxycarbonyl or dimethylamino, and $R^2$ may additionally be hydrogen, in which case $R^3$ is a 5 or 6 member heterocyclic or heteroaromatic radical; and
$R^3$ is hydrogen;
unsubstituted or substituted alkyl;
an unsubstituted or substituted saturated or monounsaturated or diunsaturated 5 or 6 member cyclic structure which, in addition to carbon atoms, may contain from one to three hetero atoms selected from the group consisting of oxygen, sulfur and nitrogen as ring members;
or an unsubstituted or substituted mononuclear or dinuclear aromatic system which, in addition to carbon atoms, may contain from one to four nitrogen atoms or from one to three hetero atoms selected from the group consisting of two nitrogen atoms and one oxygen or sulfur atom, and
$R^4$ is hydrogen, $C_1$-$C_4$-alkyl, partially or completely halogenated $C_1$-$C_4$-alkyl, halogen, cyano, nitro, dimethylamino or $C_1$-$C_6$-alkoxycarbonyl.

2. A pesticide or a fungicide, containing an effective amount of an α-arylacrylic acid derivative of the formula I

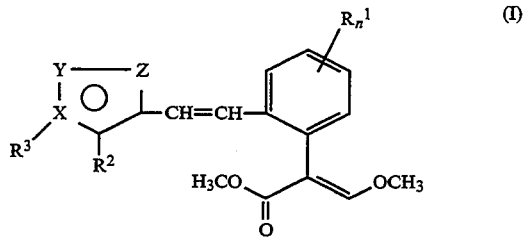

where
(a) X is C, Y is O, and Z is N; or
(b) X is C, Y is N, and Z is O; or
(c) X is N, Y is N, and Z is $CR^4$;
n is from 0 to 4
$R^1$ is nitro, cyano, halogen;
$C_1$-$C_4$-alkyl, $C_1$-$C_4$-alkoxy, partially or completely halogenated $C_1$-$C_4$-alkyl, partially or completely halogenated $C_1$-$C_4$-alkoxy or $C_1$-$C_4$-alkylthio,
or, where n is 2, 3 or 4, two adjacent substituents $R^1$ together form 1,3-butadiene-1,4-diyl, which may carry from one to four halogen atoms and/or one or two of the following groups: nitro, cyano, $C_1$-$C_4$-alkyl, $C_1$-$C_4$-alkoxy, partially or completely halogenated $C_1$-$C_4$-alkyl, partially or completely halogenated $C_1$-$C_4$-alkoxy or $C_1$-$C_4$-alkylthio;
$R^2$ is $C_1$-$C_4$-alkyl, partially or completely halogenated $C_1$-$C_4$-alkyl, halogen, cyano, nitro, $C_1$-$C_4$-alkoxycarbonyl or dimethylamino, and $R^2$ may additionally be hydrogen, in which case $R^3$ is a 5 or 6 member heterocyclic or heteroaromatic radical; and
$R^3$ is hydrogen;
unsubstituted or substituted alkyl;
an unsubstituted or substituted saturated or monounsaturated or diunsaturated 5 or 6 member cyclic structure which, in addition to carbon atoms, may contain from one to three hetero atoms selected from the group consisting of oxygen, sulfur and nitrogen as ring members;

or an unsubstituted or substituted mononuclear or dinuclear aromatic system which, in addition to carbon atoms, may contain from one to four nitrogen atoms or from one to three hetero atoms selected from the group consisting of two nitrogen atoms and one oxygen or sulfur atom, and $R^4$ is hydrogen, $C_1$-$C_4$-alkyl, partially or completely halogenated $C_1$-$C_4$-alkyl, halogen, cyano, nitro, dimethylamino or $C_1$-$C_6$-alkoxycarbonyl, and an inert additive.

3. A method for controlling pests or fungi, wherein the pests or the fungi or their habitat is or are treated with an effective amount of an α-arylacrylic acid derivative of the formula I

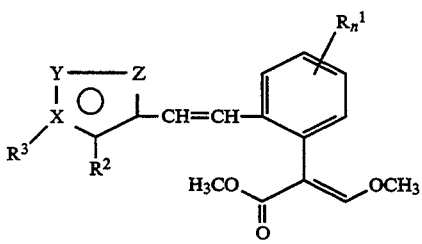

where
(a) X is C, Y is O, and Z is N; or
(b) X is C, Y is N, and Z is O; or
(c) X is N, Y is N, and Z is $CR^4$;
n is from 0 to 4
$R^1$ is nitro, cyano, halogen;
$C_1$-$C_4$-alkyl, $C_1$-$C_4$-alkoxy, partially or completely halogenated $C_1$-$C_4$-alkyl, partially or completely halogenated $C_1$-$C_4$-alkoxy or $C_1$-$C_4$-alkylthio, or, where n is 2, 3 or 4, two adjacent substituents $R^1$ together form 1,3-butadiene-1,4-diyl, which may carry from one to four halogen atoms and/or one or two of the following groups: nitro, cyano, $C_1$-$C_4$-alkyl, $C_1$-$C_4$-alkoxy, partially or completely halogenated $C_1$-$C_4$-alkyl, partially or completely halogenated $C_1$-$C_4$-alkoxy or $C_1$-$C_4$-alkylthio;

$R^2$ is $C_1$-$C_4$-alkyl, partially or completely halogenated $C_1$-$C_4$-alkyl, halogen, cyano, nitro, $C_1$-$C_4$-alkoxycarbonyl or dimethylamino, and $R^2$ may additionally be hydrogen, in which case $R^3$ is a 5 or 6 member heterocyclic or heteroaromatic radical; and $R^3$ is hydrogen;
unsubstituted or substituted alkyl;
an unsubstituted or substituted saturated or monounsaturated or diunsaturated 5 or 6 member cyclic structure which, in addition to carbon atoms, may contain from one to three hetero atoms selected from the group consisting of oxygen, sulfur and nitrogen as ring members;

or an unsubstituted or substituted mononuclear or trinuclear aromatic system which, in addition to carbon atoms, may contain from one to four nitrogen atoms or from one to three hetero atoms selected from a group consisting of two nitrogen atoms and one oxygen or sulfur atom, and $R^4$ is hydrogen, $C_1$-$C_4$-alkyl, partially or completely halogenated $C_1$-$C_4$-alkyl, halogen, cyano, nitro, dimethylamino or $C_1$-$C_6$-alkoxycarbonyl.

4. The compound of claim 1 wherein $R^2$ is $CH_3$, $CF_3$ or halogen.

5. A compound of the formula I as claimed in claim 1, wherein n is 0, $R^2$ is chlorine, $R^3$ is unsubstituted or substituted phenyl, X is C, Y is N and Z is O.

6. A compound of the formula I as claimed in claim 1, wherein n is 0, $R^2$ is trifluoromethyl, $R^3$ is unsubstituted or substituted phenyl, X and Y are each N and Z is CH.

7. A compound of the formula I as claimed in claim 1, wherein n is 0, $R^2$ is methyl, $R^3$ is unsubstituted or substituted phenyl, X is C, Y is O and Z is N.

8. The compound of claim 1 wherein $R^3$ is substituted phenyl.

9. The compound of claim 8 wherein $R^3$ is phenyl substituted by one, two or three of the substituents halogen, $C_1$-$C_4$ alkyl, $C_1$-$C_4$ haloalkyl or $C_1$-$C_4$ alkoxy.

10. The compound of claim 1 wherein X is C, Y is O, Z is N and $R^2$ is halogen.

11. The compound of claim 1 wherein X is C, Y is N, Z is O and $R^2$ is halogen.

12. The compound of claim 1 wherein X is N, Y is N, Z is $CR^4$, $R^4$ is hydrogen and $R^2$ is $CH_3$, $CF_3$ or halogen.

13. The compound of claim 1, in which $R^2$ is methyl; $R^3$ is 4-chlorophenyl; $R^4$ is methyl; n is 0; X is N; Y is N; and Z is $CR^4$.

14. An α-arylacrylic acid derivative of the formula I

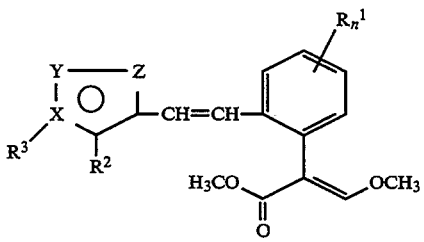

where
X is N, Y is N, and Z is $CR^4$;
n is from 0 to 4
$R^1$ is nitro, cyano, halogen;
$C_1$-$C_4$-alkyl, $C_1$-$C_4$-alkoxy, partially or completely halogenated $C_1$-$C_4$-alkyl, partially or completely halogenated $C_1$-$C_4$-alkoxy or $C_1$-$C_4$-alkylthio, or, where n is 2, 3 or 4, two adjacent substituents $R^1$ together form 1,3-butadiene-1,4-diyl, which may carry from one to four halogen atoms and/or one or two of the following groups: nitro, cyano, $C_1$-$C_4$-alkyl, $C_1$-$C_4$-alkoxy, partially or completely halogenated $C_1$-$C_4$-alkyl, partially or completely halogenated $C_1$-$C_4$-alkoxy or $C_1$-$C_4$-alkylthio;

$R^2$ is $C_1$-$C_4$-alkyl, partially or completely halogenated $C_1$-$C_4$-alkyl, halogen, cyano, nitro, $C_1$-$C_4$-alkoxycarbonyl or dimethylamino, and $R^2$ may additionally be hydrogen, in which case $R^3$ is a 5 or 6 member heterocyclic or heteroaromatic radical; and $R^3$ is hydrogen;
unsubstituted or substituted alkyl;
an unsubstituted or substituted saturated or monounsaturated or diunsaturated 5 or 6 member cyclic structure which, in addition to carbon atoms, may contain from one to three hetero atoms selected from the group consisting of oxygen, sulfur and nitrogen as ring members;

or an unsubstituted or substituted mononuclear or dinuclear aromatic system which, in addition to carbon atoms, may contain from one to four nitrogen atoms or from one to three hetero atoms selected from the group consisting of two nitrogen atoms and one oxygen or sulfur atom, and $R^4$ is hydrogen, $C_1$–$C_4$-alkyl, partially or completely halogenated $C_1$–$C_4$-alkyl, halogen, cyano, nitro, dimethylamino or $C_1$–$C_6$-alkoxycarbonyl.

15. A pesticide or a fungicide, containing an effective amount of an α-arylacrylic acid derivative of the formula I

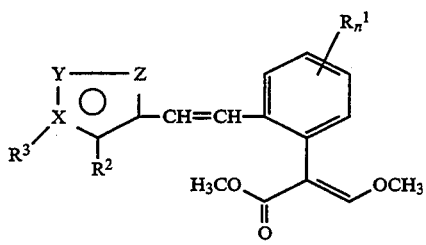

where

X is N, Y is N, and Z is $CR^4$;

n is from 0 to 4

$R^1$ is nitro, cyano, halogen;

$C_1$–$C_4$-alkyl, $C_1$–$C_4$-alkoxy, partially or completely halogenated $C_1$–$C_4$-alkyl, partially or completely halogenated $C_1$–$C_4$-alkoxy or $C_1$–$C_4$-alkylthio, or, where n is 2, 3 or 4, two adjacent substituents $R^1$ together form 1,3-butadiene-1,4-diyl, which may carry from one to four halogen atoms and/or one or two of the following groups: nitro, cyano, $C_1$–$C_4$-alkyl, $C_1C_4$-alkoxy, partially or completely halogenated $C_1$–$C_4$-alkyl, partially or completely halogenated $C_1$–$C_4$-alkoxy or $C_1$–$C_4$-alkylthio;

$R^2$ is $C_1$–$C_4$-alkyl, partially or completely halogenated $C_1$–$C_4$-alkyl, halogen, cyano, nitro, $C_1$–$C_4$-alkoxycarbonyl or dimethylamino, and $R^2$ may additionally be hydrogen, in which case $R^3$ is a 5 or 6 member heterocyclic or heteroaromatic radical; and $R^3$ is hydrogen;

unsubstituted or substituted alkyl;

an unsubstituted or substituted saturated or monounsaturated or diunsaturated 5 or 6 member cyclic structure which, in addition to carbon atoms, may contain from one to three hetero atoms selected from the group consisting of oxygen, sulfur and nitrogen as ring members;

or an unsubstituted or substituted mononuclear or dinuclear aromatic system which, in addition to carbon atoms, may contain from one to four nitrogen atoms or from one to three hetero atoms selected from the group consisting of two nitrogen atoms and one oxygen or sulfur atom, and $R^4$ is hydrogen, $C_1$–$C_4$-alkyl, partially or completely halogenated $C_1$–$C_4$-alkyl, halogen, cyano, nitro, dimethylamino or $C_1$–$C_6$-alkoxycarbonyl, and an inert additive.

16. A method for controlling pests or fungi, wherein the pests or the fungi or their habitat is or are treated with an effective amount of an α-arylacrylic acid derivative of the formula of I

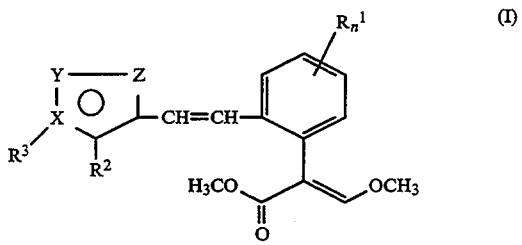

where

X is N, Y is N, and Z is $CR^4$;

n is from 0 to 4;

$R^1$ is nitro, cyano, halogen;

$C_1$–$C_4$-alkyl, $C_1$–$C_4$-alkoxy, partially or completely halogenated $C_1$–$C_4$-alkyl, partially or completely halogenated $C_1$–$C_4$-alkoxy or $C_1$–$C_4$-alkylthio, or, where n is 2, 3 or 4, two adjacent substituents $R^1$ together form 1,3-butadiene-1,4-diyl, which may carry from one to four halogen atoms and/or one or two of the following groups: nitro, cyano, $C_1$–$C_4$-alkyl, $C_1$–$C_4$-alkoxy, partially or completely halogenated $C_1$–$C_4$-alkyl, partially or completely halogenated $C_1$–$C_4$-alkoxy or $C_1$–$C_4$-alkylthio;

$R^2$ is $C_1$–$C_4$-alkyl, partially or completely halogenated $C_1$–$C_4$-alkyl, halogen, cyano, nitro, $C_1$–$C_4$-alkoxycarbonyl or dimethylamino, and $R^2$ may additionally be hydrogen, in which case $R^3$ is a 5 or 6 member heterocyclic or heteroaromatic radical; and $R^3$ is hydrogen;

unsubstituted or substituted alkyl;

an unsubstituted or substituted saturated or monounsaturated or diunsaturated 5 or 6 member cyclic structure which, in addition to carbon atoms, may contain from one to three hetero atoms selected from the group consisting of oxygen, sulfur and nitrogen as ring members;

or an unsubstituted or substituted mononuclear or trinuclear aromatic system which, in addition to carbon atoms, may contain from one to four nitrogen atoms or from one to three hetero atoms selected from a group consisting of two nitrogen atoms and one oxygen or sulfur atom, and $R^4$ is hydrogen, $C_1$–$C_4$-alkyl, partially or completely halogenated $C_1$–$C_4$-alkyl, halogen, cyano, nitro, dimethylamino or $C_1$–$C_6$-alkoxycarbonyl.

17. The compound of claim 14 wherein n is 0.

18. The compound of claim 14 wherein $R^2$ is alkyl or haloalkyl.

19. The compound of claim 18 wherein $R^2$ is $CF_3$.

20. The compound of claim 14 wherein $R^3$ is substituted or unsubstituted phenyl.

21. The compound of claim 17 wherein $R^3$ is monohalophenyl.

22. The compound of claim 20 wherein $R^3$ is dihalophenyl.

23. The compound of claim 14 wherein $R^2$ is trifluoromethyl; $R^3$ is 4-chlorophenyl; $R^4$ is hydrogen; and n is 0.

24. The compound of claim 14 wherein $R^2$ is trifluoromethyl; $R^3$ is 2,4-dichlorophenyl; $R^4$ is hydrogen; and n is 0.

* * * * *